United States Patent [19]

Hausweiler et al.

[11] 4,059,492
[45] Nov. 22, 1977

[54] PROCESS FOR THE PURIFICATION OF WASTE FROM ACRYLONITRILE PRODUCTION

[75] Inventors: Arnold Hausweiler, Zons; Adolf Mayer, Dormagen; Feliks Bitners, Leverkusen, all of Germany

[73] Assignees: Erdolchemie GmbH, Cologne; Bayer Aktiengesellschaft, Leverkusen, both of Germany

[21] Appl. No.: 682,555

[22] Filed: May 3, 1976

Related U.S. Application Data

[63] Continuation-in-part of Ser. No. 544,458, Jan. 27, 1975, abandoned, which is a continuation of Ser. No. 466,350, May 2, 1974, abandoned, which is a continuation of Ser. No. 188,395, Oct. 12, 1971, abandoned.

[30] Foreign Application Priority Data

Oct. 15, 1970   Germany .............................. 2050722

[51] Int. Cl.$^2$ .......................... B01D 1/00; B01D 3/34
[52] U.S. Cl. ......................................... 203/11; 203/25; 203/DIG. 3; 203/73; 203/38; 203/59; 203/92; 203/96; 210/64; 260/465.9
[58] Field of Search ...................... 203/10, 11, DIG. 3, 203/DIG. 19, 71–85, 98, 99, 25, 26, 27, 95–97, 92, 38, 59; 260/465.9, 465.3; 210/64; 424/325, 329

[56] References Cited

U.S. PATENT DOCUMENTS

| | | | |
|---|---|---|---|
| 2,247,711 | 7/1941 | Ralston et al. | 210/64 |
| 3,254,024 | 5/1966 | Huckins et al. | 203/25 |
| 3,352,764 | 11/1967 | Tyler | 203/84 |
| 3,399,120 | 8/1968 | Lovett | 203/84 |
| 3,433,822 | 3/1969 | Hausweiler et al. | 260/465.3 |
| 3,442,771 | 5/1969 | Jordan et al. | 203/33 |
| 3,445,347 | 5/1969 | Borrel et al. | 203/99 |
| 3,468,624 | 9/1969 | Miller | 260/465.9 |
| 3,636,068 | 1/1972 | Lovett et al. | 203/DIG. 3 |
| 3,694,322 | 9/1972 | Ikeda et al. | 203/25 |
| 3,734,943 | 5/1973 | Fitzgibbons et al. | 260/465.9 |

Primary Examiner—Wilbur L. Bascomb, Jr.
Attorney, Agent, or Firm—Burgess, Dinklage & Sprung

[57] ABSTRACT

Waste water resulting from the production of acrylonitrile by gas phase oxidation of propylene and ammonia with oxygen as washing water in the recovery section is purified by treating the waste water with 0.4 to 1 ton of steam per ton of waste water in a detoxification column attached to or following the separation column (for the separation of acetonitrile and acrylonitrile from the waste water in the acrylonitrile process) at a temperature from 100° to 125° C, at a pressure of 0 to 2 (gauge) atmospheres; separating the non-volatile resinous organic compounds from the thus treated waste water in an evaporator and using the vapors from the top of said evaporator to heat the said separation column and detoxification column; and optionally adding an organic amine to said distillation column or to said evaporator.

20 Claims, 3 Drawing Figures

PROCESS FOR THE PURIFICATION OF WASTE FROM ACRYLONITRILE PRODUCTION

CROSS REFERENCE TO RELATED APPLICATIONS

This application is a continuation-in-part of application Ser. No. 544,458 filed Jan. 27, 1975 and now abandoned which, in turn, is a continuation application of Ser. No. 466,350 filed May 2, 1974, abandoned, which, in turn, is a continuation of Ser. No. 188,395 filed Oct. 12, 1971, abandoned.

The present invention concerns the purification of waste water which has been used in plants for the production of acrylonitrile by gas phase oxidation of propylene and ammonia with oxygen, as washing water in the recovery section for removing the reaction products from the reaction gas and for separating acrylonitrile and acetonitrile.

In all processes for the preparation of acrylonitrile from propylene, ammonia and air, there are formed in the reactor, besides the acrylonitrile desired, considerable amounts of by-products such as hydrocyanic acid, acetonitrile and water. The reaction gas leaving the reactor is conducted to a working-up system consisting of washing and distillation columns, where the water-soluble components in the reaction gas are removed with water. Hydrocyanic acid and acrylonitrile, on the one hand, and acetonitrile, on the other, are separated out of the aqueous solution. Besides the washing water, which is recycled, there also remains excess water which has to be discharged from the system as waste water (DOS 1,920,083, Austrian Pat. No. 280,235, U.S. Pat. No. 3,442,771, Belg. Pat. No. 593,630, Belg. Pat. No. 690,877, U.S. Pat. No. 3,399,120).

In each case, the same amount of water as has been produced in the form of steam in the reactor chiefly as a result of the oxidation reaction has to be flushed out of the recovery system.

A waste water obtained as described in the example in DOS 1,920,083 and Austrian Pat. No. 280,235 (see Example 3 of the present application) was investigated. It contained indeed only residual traces of acrylonitrile, acetonitrile and hydrogen cyanide but considerable quantities of bound cyanide, for example in the form of addition compounds of hydrogen cyanide with ketones and aldehydes, as well as high-boiling and resinous organic compounds.

The inhibiting effect of the impurities contained in this water on the biological degradation, even at high dilution, is extremely high and the maximum attainable total degradation is about 40% which is totally insufficient.

In DOS 1,920,083 a method is given for purifying the waste water by evaporating it to 1/50 of its volume and burning the residue. This method, however, achieves separation only of the resinous components but not of the distillable compounds or the very toxic compounds produced during the distillation by, for example, decomposition of cyanohydrins. These compounds collect in the condensate and prevent biological purification. (See Example 3 of the present application). Moreover, this method of purifying the waste water would be prohibitively expensive; according to the example in DOS 1,920,083, 5 $t$ of steam per $t$ of acrylonitrile produced would have to be used for evaporating the waste water, while the resulting steam, owing to the distillation under a reduced pressure of 0.1 atm. cannot be used for heating columns.

Obvious methods for detoxifying the waste water such as chlorination and treatment with ozone etc. are not successful; it is true that detoxication can be achieved by alkaline hydrolysis but this causes a black coloration of the water. Processes such as extraction and high pressure oxidation (so-called wet burning) can be successfully employed but are too expensive.

A process has now been found for the purification of waste water which contains volatile and toxic and high-boiling and resinous organic compounds from plants for the production of acrylonitrile by gas-phase oxidation of propylene and ammonia with oxygen in the presence of a solid catalyst, characterized in that the waste water, in order to remove and destroy toxic compounds, is treated in a detoxification column having 7 to 20 distribution baffles which is attached to the lower end of a column for the separation of acetonitrile from the waste water at a temperature in the range of from 100° to 125° C and a pressure in the range of 0 to 2 gauge with from 0.4 to 1.0 $t$ steam per $t$ waste water flowing to the detoxification column, optionally after addition of from 0.005 to 0.2 wt. % of an organic amine, that the bottom product of the detoxification column, optionally after the addition of an organic amine, is passed into a evaporation vessel equipped with a reboiler heated by steam in which the bottom product of the detoxification column is substantially vaporized and the vapors are used for indirectly heating the detoxification column as well as the column for separating acetonitrile from the waste water and after condensation are discharged directly or after biological purification into a flowing water system, and the aqueous solution remaining in the bottom of the vaporizer with from 1 to 60 wt. % high-boiling and resinous organic compounds and the organic basic compounds optionally added to the detoxification column or to the evaporation vessell is drawn off.

Any organic amine may be used the boiling point of which is above 170°C. The amine added via (11) or (12) (see FIG. 1) should be non-volatile or only slightly volatile under the operating conditions because it should not be present in appreciable amounts either in the crude nitrile drawn off at the head of 1 or in the purified waste water taken off at 9. Any primary, secondary or tertiary amine or quaternary ammonium base is suitable provided the amino group is not directly attached to an aromatic nucleus or the molecule does not contain strongly acidic groups such as a sulphonic acid residue etc. High-boiling residues from processes for the preparation of aliphatic amines such as ethylenediamine or amino alcohols such as ethanolamine are particularly suitable.

For example, the following amines can be used: 1-amino-2-methyl-hexane, 3-amino-2, 4-dimethyl-pentane, 3-amino-2, 5-dimethyl-hexane, 1-amino-2-methyl-nonane, 3-aminomethylundecane, 1-amino-octadecane, 1,14-diamino-3, 6,9,12-tetraazatetradecane, tripropylene-(1,2)-tetramine, trimethyl-hexamethylenediamine-(1,6) (isomeric mixture), 2,2-dihydroxy-diethylamine, 2-[methyl-(3-amino-propyl)-amino]-ethanol-(1), (3-amino-propyl)-(2-ethyl-hexyl)-ether, 2-amino-2-methyl-propadiol-(1,3), N,N'-bis-(1-methyl-1-cyanoethyl)-hydrazine, 1-cyclo-hexylaminopropanol-(2), N-(2-aminoethyl)-piperazine, 4,4'-diaminodicyclohexylmethane, 1-(2-aminoethyl-amino)-naphthalene and methyldibenzylamine.

The process of the invention thus consists of a combination of three features:

a. Separation of the resinous and high-boiling compounds by evaporation of water and use of the vapors for indirectly heating the detoxification column and the column for separating the acetonitrile from the waste water.

b. Previous detoxification of the waste water by treatment with a defined amount of steam.

c. Optional detoxification by the addition of organic amines during the steam treatment or during the evaporation of the water (see the effect of organic amines in Example 2).

It was surprising and could not be foreseen that a waste-water detoxification satisfactory in every respect could be achieved merely by a more intensive steam treatment, optionally in the presence of an organic amine.

A particular technical and economic advantage of the process consists in the synchronization of waste-water production and steam requirement of the treatment system. With increasing waste-water production at the bottom of the acrylonitrile-acetonitrile separating columns, the steam requirement of the system increases; at the same time, however, the waste-water evaporation is increased and more steam flows back to the detoxification and separating columns. For those plants which must carry out a purification of the waste-water, the process of the invention offers an optimum solution as regards economy and reliability.

The process of the invention can be used for all known or conceivable ways of operating the production of acrylonitrile.

BRIEF DESCRIPTION OF DRAWINGS

Referrin to the drawings herein:

FIG. 1 shows the basic elements of the process.

Figure 1:
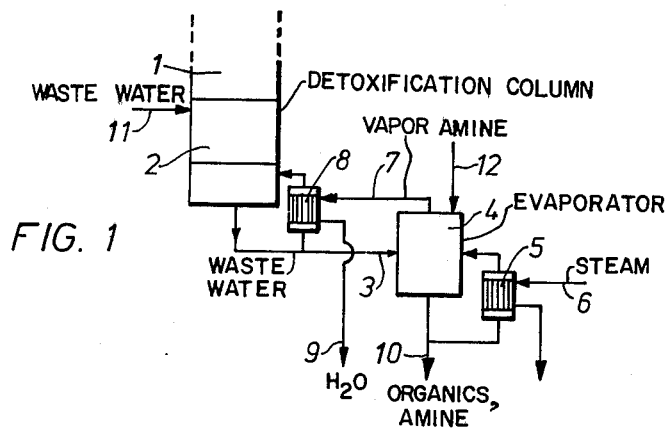
FIG. 1 is a flow diagram showing the basic elements of the process wherein waste water containing contaminants is charged to a detoxification zone, withdrawn and fed to an evaporator, vaporized therein, fed to a reboiler, a portion of the water collected and a portion introduced in indirect heat exchange to the detoxification zone.

From the bottom of column 1, in which the separation of acetonitrile or of acrylonitrile, acetonitrile and hydrogen cyanide from the wash water is carried out, waste water containing 0.2 to 2.0 wt. % resinous polymers;

200 to 1000 ppm cyanide ions, i.e. combined hydrogen cyanide;

400 to 3000 ppm maleic, fumaric and succinic acid dinitriles;

up to 2000 ppm unidentified compounds passes into the detoxification column 2 containing 7 to 20 baffles. Columns 1 and 2 can be arranged in a single unit or separately. Both are heated indirectly with steam by means of the reboiler 8.

The temperature in the bottom of 2 is 100° to 125° C, preferably 110° to 120° C.

The pressure in 2 is 0 to 2 atm gauge., preferably 0.4 to 1 atm gauge.

The steam loading of 2 is from 0.4 to 1 $t$ steam/$t$ waste water flowing to the detoxification column, preferably from 0.5 to 0.8 $t$.

0.005 to 0.2 wt. %, preferably 0.01 to 0.1 wt. % of an organic amine can be added to the waste water via 11. Under the reaction conditions this amine is not, or is only to a slight extent volatized from the bottom of the column 2, an evaporization vessel a 4 of a reboiler 5.

From 2 the waste water passes via 3 to the vessel which is equipped with the reboiler 5. 5 is heated by steam 6.

The vapors emerging from 4 are led via 7 to the reboiler 8 where they are condensed while releasing energy and then pass via 9 directly into a flowing water system or first through a biological treatment plant. Through 12 0.005 to 0.2, preferably 0.01 to 0.1 wt. %, of an organic amine which, under the process conditions, is not or is only to a slight degree volatile can be added to (4). From (4) a concentrate containing up to 60 wt. % of high-boiling and resinous organic compounds is withdrawn through 10 and passed, for example, to an incinerator. Alternatively, the concentrate can be converted to a dough with, for example, brown-coal ash and dumped in heaps.

The detoxification column 2 does not have to be operated as a single unit together with column 1; it can be a separate column connected to 1 by a steam pipe. Furthermore, the detoxification column 2 and the evaporating equipment 4 can be combined in one unit in such a way that 4 and 2 are placed one above the other in a single apparatus with a horizontal separating floor. (The numbers refer to FIG. 1).

Figure 2:
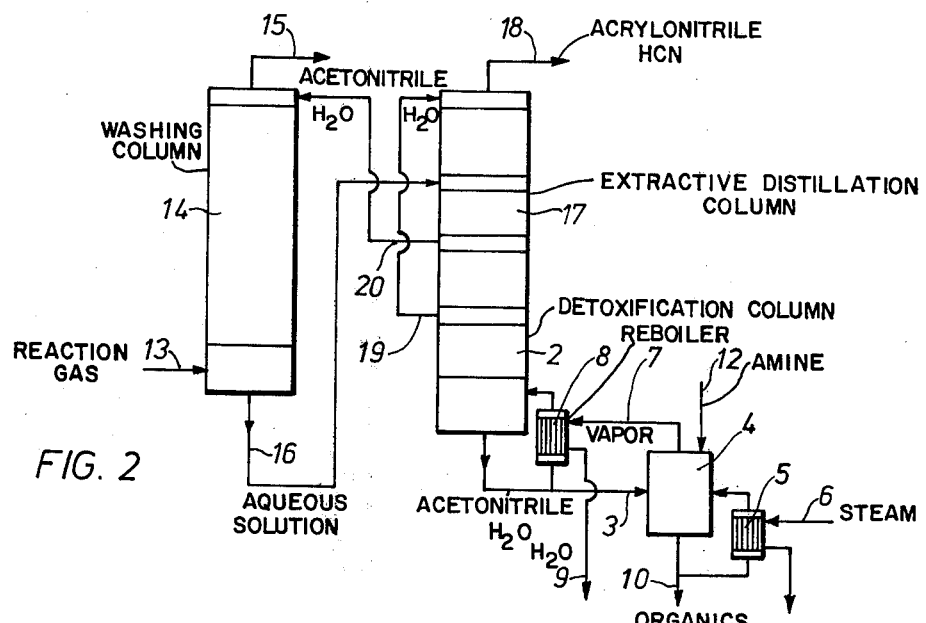
FIG. 2 is a flow diagram showing a further embodiment wherein an extracted distillation column is disposed over the detoxification column which are fed with an aqueous solution resulting from washing the reaction products of an acrylonitrile-acetonitrile process.

FIG. 2 shows the combination of the process of the invention as described in FIG. 1, with one way of carrying out the acrylonitrile process.

Acrylonitrile, acetonitrile and hydrogen cyanide are removed with water from a reaction gas 13 in a washing column 14; the aqueous solution passes through 16 to an extractive distillation column 17 from the head 18 of which acrylonitrile and hydrogen cyanide are expelled and from the bottom of which water and acetonitrile pass through 20 to the absorber 14 where acetonitrile is blown out by the inert gas component of the washed reaction gas leaving the column via 15 while the water is used for washing. Water free of acetonitrile is fed as extraction water through 19 to the head of 17. The excess water arrives at 2 and is further dealt with as shown in FIG. 1. In the process the total steam requirement of 17 and 2 is covered by the waste steam coming through 7 from 4.

The examples quoted do not exhaust the possible applications of the process of the invention. It can be used in all acrylonitrile processes in which a waste water almost free of acrylonitrile and acetonitrile emerges at the exit of a column or system of columns.

EXAMPLE 1a (the references are to FIG. 1)

From the lowest level of an acetonitrile-expelling column 1 which is attached to the top of a detoxification column 2 containing 16 material-exchange baffles, flows to the uppermost baffle 36 t/h aqueous waste carrying 117.8 kg/h hydrogen cyanide (free and combined);

0.3 kg/h acrylonitrile;
2.4 kg/h acetonitrile;
30.4 kg/h maleic acid dinitrile;
50.2 kg/h fumaric acid dinitrile;
22.3 kg/h succinic acid dinitrile; and
205.2 kg/h unknowns + polymers.

The column is heated at the base by means of a reboiler 8. The bottom temperature is 113° C and the pressure 1.6 atm. 19 t detoxified waste water is withdrawn hourly through the pipe 3 from the bottom of column 2 with 0.6 kg/h hydrogen cyanide;
27.6 kg/h maleic acid dinitrile;
44.8 kg/h fumaric acid dinitrile;
19.7 kg/h succinic acid dinitrile; and
176.2 kg/h unknowns and polymers and fed into the evaporation vessel 4 with the reboiler 5. The stream leaving the detoxification column 2 amounting to about 18 t/h contains besides water 0.3 kg/h acrylonitrile;
2.4 kg/h acetonitrile; and
117.2 kg/h hydrogen cyanide and is passed to the lowest exchanger baffle of the acetonitrile expeller 1. The reboiler 5 is heated with about 18 t/h heating steam at 6 atm. pressure. The pressure in the steam space of 4 is 2.6 atm. About 18 t process steam flows hourly through pipe 7 to the reboiler 8, is condensed therein and led off through a pipe 9 as purified waste water. This is colorless and odorless while only about 2 ppm hydrogen cyanide can still be detected by analysis. Through pipe 10

27.6 kg/h maleic acid dinitrile;
44.8 kg/h fumaric acid dinitrile;
19.7 kg/h succinic acid dinitrile;
176.2 kg/h unknowns + polymers; and
691.3 kg/h water are conveyed to an incinerator.

The process is arranged differently if the acrylonitrile plant, as described in U.S. Pat. No. 3,433,822, is operated with a gas washer to remove catalyst dust and resinous polymers. This gas scrubber, for example in a plant for the production of 50,000 tons p.a. acrylonitrile, has a requirement for 7 to 8 tons of water per hour. This water can be drawn through 10 from the waste water purification unit. The polymers dissolved in it pass through the gas scrubber to the incinerator. From 19 t waste water only 11 to 12 i t have still to be vaporized in the reboiler 5 and 7 to 8 t fresh steam in addition to the process steam from 4 is introduced into the reboiler 8.

If in practice cases arise in which the waste water produced at the bottom of 2 is greater than the amount of steam required by the column, then the process steam leaving 4 can be used both for heating 2 as well as for heating an additional distillation column.

Whether the waste water withdrawn through 9 should be discharged directly into a water course or first biologically purified depends on the local conditions of the particular acrylonitrile plant as well as the official regulations governing the composition of waste water.

The waste water described in Example 1 (withdrawn through 9) has a BOD-value of from 50 to 300 ppm and can, if required be biologically purified without any difficulty.

EXAMPLE 1b

In carrying out the process as in Example 1a, the value in Table 1 indicate the effectiveness of column 2 as regards the hydrogen cyanide content at the exit (3) as a function of the number of exchange baffles in the detoxification column (2):

Table 1

| Number of exchange baffles in column (2) | Kg/h hydrogen cyanide (free and combined) in feed to (2) | Kg/h hydrogen cyanide (free and combined) in outflow from (2) |
| --- | --- | --- |
| 6 | 117.8 | 9.5 |
| 8 | 117.8 | 3.4 |
| 12 | 117.8 | 1.3 |
| 16 | 117.8 | 0.6 |
| 20 | 117.8 | 0.35 |
| 24 | 117.8 | 0.30 |

EXAMPLE 2 (The references are to FIG. 1)

The experiment described here shows the effect of the addition of amine to the detoxification column 2.

As in Example 1a, 36 t/h waste water with the composition there described was withdrawn from the lowest baffle of column 1 and led to the top of 2. Detoxification column 2 was heated by a reboiler 8, the temperature at the bottom was 113° C and the pressure 1.6 atm. From the bottom 22 t/h of only partially detoxified waste water was withdrawn containing 9.7 kg/h hydrogen cyanide (combined);
104 kg/h dinitriles of C4—acids; and
186 kg/h unknowns and polymers and passed to the vessel 4 which was heated indirectly by a reboiler. 14 t/h steam left column 2 and was led to the lowest baffle of 1. The reboiler 5 was heated with about 14 t/h steam at 6 atm. The pressure in the steam space was 2.6 atm. About 14 t/h process steam flowed to the reboiler 8, was there condensed and drawn off through 9 as waste water still having 7.8 kg/h hydrogen cyanide. Its toxicity was still so great that biological purification succeeded only after dilution 1:20 with fresh water. Through pipe 10 8 t/h of a stream taken off with 81 kg dinitriles of C4—acids; and
179 kg unknowns and polymers.

The same experiment was then carried out with the addition of 3 kg/h of a high-boiling residue from the preparation of ethanolamine to the top baffle of column 2.

At the bottom of the column 22 t/h were withdrawn with 0.47 kg hydrogen cyanide
91 kg dinitriles of C4—acids; and
198 kg unknowns and polymers and, as described above, treated further. The waste water which was drawn off through 9 contained only traces of hydrogen cyanide and could, be biologically purified undiluted without difficulty.

In a further experiment the amine (residue from the preparation of ethanolamine) was added not to the top of column 2 but to the evaporator vessel 4. The waste water withdrawn through 9 contained only from 5 to 10 ppm hydrogen cyanide and could be biologically purified without dilution.

EXAMPLE 3

By reworking the example described in Austrian Pat. No. 280,235, a waste water of the following composition was obtained from the heating chamber of the acetonitrile expeller described there:

0.7 wt. % resinous polymers;
280 ppm fumaric dinitrile;
850 ppm maleic acid dinitrile;
390 ppm cyanide ions;
970 ppm succinic acid dinitrile; and about
600 ppm unidentifiable organic compounds The remainder was water. The BOD-value was 5,500 and the COD-value 10,500. The waste water was medium brown in color and proved very highly toxic in the biological purification process.

It could only be treated in 1:50 dilution with clean water; in that case the COD-value decreased to 48% of the original value after 24 hours residence time in the biological treatment plant.

This waste water was, as described in the example in Austrian Pat. No. 280,235, concentrated under a vacuum of 0.1 atm. to 1/50 of its original volume. The residue which contained suspended oily drops and solid resins was not investigated further. The process steam condensate contained the following organic compounds:

440 ppm cyanide ions;
150 ppm fumaric acid dinitrile;
330 ppm maleic acid dinitrile;
450 ppm succinic acid dinitrile; and about
520 ppm unidentifiable organic compounds The BOD-value of the condensate was 1,200 to 1,300. The waste water showed very high toxicity in the biological purification and could only be treated at dilutions of at least 1:30 to 1:35 with clean water. In that case the BOD-value decreased within 24 hours to 32% of the original value.

Figure 3:
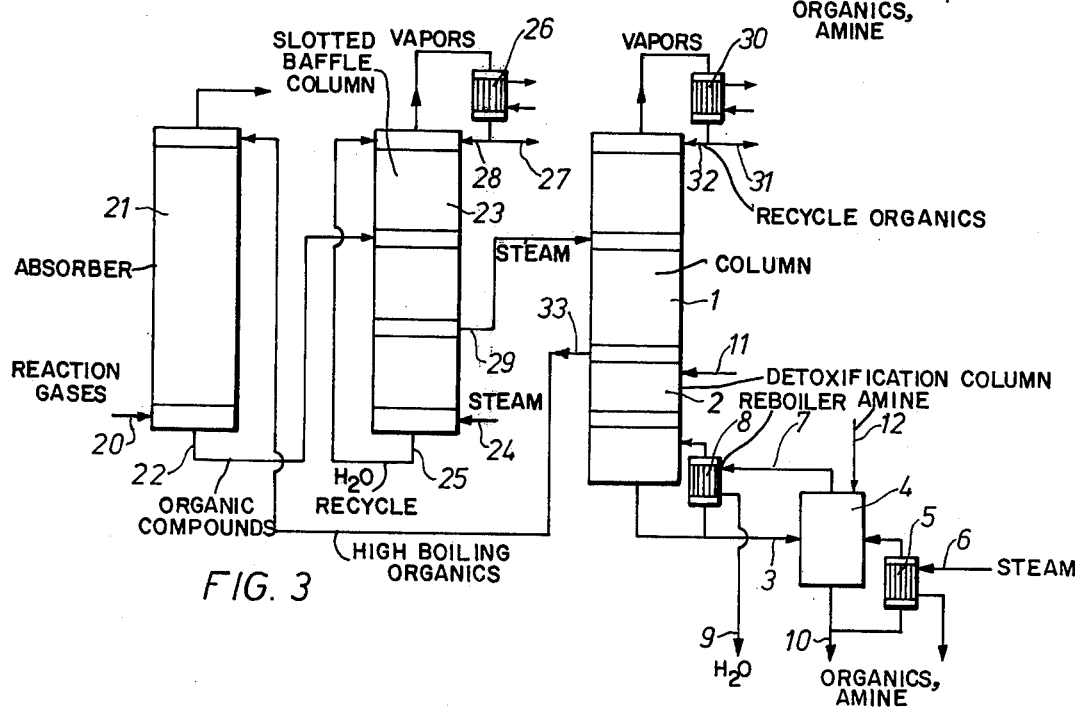
FIG. 3 is a flow diagram similar to FIG. 2 wherein steam from a slotted baffle column is introduced into the distillation column, the contents of said slotted baffle column originating from an absorber in which reaction gases are washed.

EXAMPLE 4 (The references are to FIG. 3)

In this example the waste water purification process of the present invention is combined with the process described in Austrian Pat. No. 280,235.

Reaction gases 20 containing 176 g water, 135 g acrylonitrile, 16 g acetonitrile and 21 g other organic compounds together with about 800 g inert gas were washed in an absorber column 21 containing fillers and having a diameter of 100 mm and filling depth of 3 m with 6000 g water and 5 g acetonitrile/hour at 15° C.

From the bottom of the absorber 135 g acrylonitrile, 20 g acetonitrile, 6180 g water and 38 g other organic compounds were withdrawn 22 per hour and passed at 88° C to the 30th baffle of a slotted baffle column 23 having altogether 49 baffles and a diameter of 60 mm which was heated by 500 g direct steam 24 per hour. From the bottom of this column 3000 g water per hour was withdrawn and recycled 25 at 68° to the top baffle. The vapors emerging from the head of the column in 26 were condensed. 133 g acrylonitrile, 7 g water and 15 g of other organic compounds per hour were withdrawn 27 from the condensate and 41 g water, 153 g acrylonitrile and 19 g other organic compounds per hour passed back 28 to the column. From the 20th baffle of the column from below a side stream 29 consisting of 6671 g water, 2 g acrylonitrile, 20 g acetonitrile and 23 g other organic compounds per hour was withdrawn and fed into a column system (1 and 2) in order to separate the acetonitrile and detoxify the waste water. This slotted baffle column had 45 baffles, a diameter of 6 cm. and was indirectly heated by steam using a reboiler 8. The side stream was introduced at the 35th baffle counting from the bottoms; there the temperature was 97° C. The vapors emerging from the head were condensed in 30 and after that divided into two streams, 35 g water, 2 g acrylonitrile and 15 g acetonitrile were withdrawn 31; 17 g water, 8 g acrylonitrile, 64 g acetonitrile and 4 g other organic compounds per hour were recycled 32 to the column. At the 15th baffle 6000 g water, 5 g acetonitrile and 17 g high-boiling organic compounds per hour were withdrawn 33 hourly and fed at 15° to the head of the absorber. At the 14th baffle an aqueous solution of 0.5 g of a residue from the preparation of ethylenediamine boiling above 170° C was introduced per hour through 11. From the bottom of 2 667 g per hour of detoxified water which contained 32 ppm cyanide ions, about 2000 ppm dinitriles of succinic, maleic and fumaric acids, 7000 ppm resinous polymers as well as 87 ppm unidentifiable organic compounds were withdrawn through 3. The bottom temperature in the column was 112° C and the pressure 1.52 atm. This liquid extracted from the bottom was introduced into evaporation vessel 4 equipped with a reboiler 5 which was indirect heated with about 700 g heating steam 6 per hour at 6 atm.

The pressure in the vapor space was 2.7 atm. From the vapor space about 650 g steam flowed per hour through 7 to the reboiler of the detoxification column and after condensation in 8 was removed. This condensate contained 3 ppm cyanide ions, 150 ppm dinitriles of succinic, maleic and fumaric acids and 10 ppm unidentifiable organic compounds. This water can be purified biologically without dilution and then has a BOD-value of less than 10 ppm. From the bottom of the evaporator 4 about 17 g per hour of water, polymeric and highboiling organics and the amine added for detoxification were withdrawn through 10 and passed to an incinerator.

What is claimed is:

1. Process for the purification of waste water from a process for preparing acrylonitrile by the gas phase oxidation of propylene and ammonia with oxygen in admixture with solid catalyst wherein water is used for the separation of acrylonitrile from the reaction mixture, said waste water being substantially free of acrylonitrile, acetonitrile and hydrogen cyanide and containing volatile and toxic and high-boiling and resinous organic compounds, which comprises:

i. treating said waste water with steam at a temperature between 100° and 125° C and at a pressure of from 0 to 2 atmospheres gauge, in a detoxification column containing at least 7 distribution baffles, removing volatile toxic materials as the distillate and recovering treated waste water as the bottoms product, said steam being generated in the botom of said detoxification column by indirect heating with steam produced in the following step (iv) at the rate of 0.4 to 1.0 ton of steam per ton of waste water flowing into said detoxification column;

ii. removing the so treated waste water from said detoxification column and passing it into an evaporator vessel;

iii. vaporizing a major portion of the treated waste water from the detoxification column in said evaporation vessel;

iv. recovering steam as the head product from said evaporation vessel and using said head product to generate steam in the bottom of said detoxification column by indirect heat exchange with the contents of said detoxification column, for said steam treatment; and v. removing an aqueous solution of said organic compounds as the bottoms product from said evaporation vessel.

2. Process is claimed in claim 1 wherin the number of baffles in said ditoxification column is from 7 to 20.

3. Process as claimed in claim 1 wherein the bottoms product from said evaporation vessel comprises an aqueous solution containing from 1 to 60 weight percent of high-boiling and of resinous organic compounds and is withdrawn from the system.

4. Process as claimed in claim 1 wherein from 0.005 to 0.2 weight percent of an organic amine, based on the waste water, is added to the waste water prior to or during steam treatment in said detoxification column.

5. Process as claimed in claim 1 wherein from 0.005 to 0.2 weight percent of an organic amine, based on the waste water, is added to the waste water emanating from the bottom of said detoxification column.

6. Process as claimed in claim 4 wherein said amine is substantially non-volatile under the operating conditions used in said acrylonitrile production process.

7. Process as claimed in claim 4 wherein additional amine is also added to the waste water emanating from the bottom of said detoxification column.

8. Process as claimed in claim 4 wherein said amine has a boiling point above 170° C.

9. Process as claimed in claim 1 wherein the steam treatment in said detoxification column is carried out at a temperature of from 110° to 120° C and at a pressure of 0.4 to 1 atmospheres gauge.

10. Process as claimed in claim 1 wherein the steam is supplied at a rate of from 0.5 to 0.8 tons of steam per ton of waste water.

11. Process for the purifiction of waste water which contains volatile and toxic and high-boiling and resinous organic compounds from a production plant for acrylonitrile by gas-phase oxidation of propylene and ammonia with oxygen in the presence of a solid catalyst, wherein the waste water, in order to remove and destroy the toxic compounds, is treated in a detoxification column having from 7 to 20 distribution baffles which is attached to the lower end of a column for the separation of acetonitrile from the waste water at a temperature of from 100° to 125° C and a pressure of from 0 to 2 atm. gauge with from 0.4 to 1.0 t steam per t of waste water flowing to the detoxification column, and, further, wherein the sump effluent of the detoxification column is passed into an evaporation vessel and substantially evaporated, the vapors are used for heating the detoxification column and the column for separating acetonitrile from the wash water and are discharged into a flowing water system and wherein the resulting aqueous solution in the evaporation vessel is drawn off together with from 1 to 60 wieght percent of high-boiling and resinous organic compounds.

12. Process as claimed in claim 11 wherein from 0.005 to 0.2 weight percent of an organic amine is added to the waste water before treatment in the detoxification column.

13. Process as claimed in claim 11 wherein an organic amine is added to the waste water after the treatment in the detoxification column and prior to the evaporation step.

14. Process as claimed in claim 11 wherein the vapors from the evaporation vessel are further purified by biological means before being discharged into a flowing water system.

15. Process as claimed in claim 11 wherein the treatment in the detoxification column is carried out at a temperature of from 110° to 120° C.

16. Process as claimed in claim 11 wherein the treatment in the detoxification column is carried out at a pressure of from 0.4 to 1 atm gauge.

17. Process as claimed in claim 11 wherein from 0.5 to 0.8 t of steam per t of waste water is flowing to the detoxification column.

18. Process as claimed in claim 11 wherein the detoxification column is operated separately.

19. Process as claimed in claim 11 wherein the detoxification column and evaporation vessel are combined in one unit so that the units are arranged one above the other in a single apparatus with a horizontal separating floor.

20. A process according to claim 19 wherein the waste water is treated with 0.005 to 0.2 weight percent organic amine in said evaporation vessel.

* * * * *

UNITED STATES PATENT AND TRADEMARK OFFICE
CERTIFICATE OF CORRECTION

PATENT NO. : 4,059,492
DATED : November 22, 1977
INVENTOR(S) : Arnold Hausweiler et al It is certified that error appears in the above-identified patent and that said Letters Patent are hereby corrected as shown below:

[73] Assignees, Title page, "Erdolchemie" should read -- Erdölchemie --.

[57] Abstract, Title page, last line, "distillation" should read -- detoxification --.

Column 2, line 21, insert -- atm. -- after "2".

Column 2, line 39, "vessell" should read -- vessel --.

Column 4, line 14, delete "a" before "4".

Column 5, line 19, "stream" should read -- steam --.

Column 5, line 49, delete "i" before "t".

Column 6, line 4, "value" should read -- values --.

Column 6, line 42, insert -- was -- before "taken".

Column 8, line 52, "botom" should read -- bottom --.

Column 9, line 5, "ditoxification" should read -- detoxification --.

Column 9, line 34, "purifiction" should read -- purification --.

Signed and Sealed this

Thirtieth Day of May 1978

[SEAL]

Attest:

RUTH C. MASON
Attesting Officer

LUTRELLE F. PARKER
Acting Commissioner of Patents and Trademarks